United States Patent [19]

Noiles

[11] 4,219,893
[45] Sep. 2, 1980

[54] PROSTHETIC KNEE JOINT

[75] Inventor: Douglas G. Noiles, New Canaan, Conn.

[73] Assignee: United States Surgical Corporation, Norwalk, Conn.

[21] Appl. No.: 831,095

[22] Filed: Sep. 1, 1977

Related U.S. Application Data

[63] Continuation-in-part of Ser. No. 605,208, Aug. 15, 1975, abandoned.

[51] Int. Cl.² ............................................... A61F 1/24
[52] U.S. Cl. ..................................... 3/1.911; 3/1.91; 128/92 C
[58] Field of Search ................................. 3/1.9–1.913, 3/1; 128/92 C, 92 CA

[56] References Cited

U.S. PATENT DOCUMENTS

| 3,696,446 | 6/1974 | Bousquet et al. | 3/1.911 |
| 3,813,700 | 6/1974 | Tavernetti et al. | 3/1.911 X |
| 3,869,729 | 3/1975 | Attenborough | 3/1.91 |
| 3,869,731 | 3/1975 | Waugh et al. | 3/1.911 |
| 3,909,854 | 10/1975 | Martinez | 3/1.911 |
| 3,918,101 | 11/1975 | Lagrange et al. | 3/1.911 |

FOREIGN PATENT DOCUMENTS

| 2122390 | 1/1973 | Fed. Rep. of Germany | 3/1.911 |
| 2220845 | 3/1973 | Fed. Rep. of Germany | 3/1.911 |
| 2154338 | 5/1973 | Fed. Rep. of Germany | 3/1.911 |
| 2334265 | 1/1975 | Fed. Rep. of Germany | 3/1.911 |

Primary Examiner—Ronald L. Frinks
Attorney, Agent, or Firm—Fleit & Jacobson

[57] ABSTRACT

A prosthetic knee joint of the hinged type which permits rotation of the bones in two planes and has means for attaching the device to the bones as well as coupling means. The attaching means for the tibia is in the form of a flanged sleeve in which a flanged stem element is adapted to be rotatably received. The stem element and the attaching means for the femur are coupled together so that they are permitted to undergo relative rotation in the plane of flexion. The rotation of the stem in the sleeve about the axis of the shaft of the tibia permits rotational movement of the pair of bones in a second (axial) plane. The stem is free to distract from the sleeve while maintaining alignment to insure proper reengagement. Bearing surfaces on the stem and sleeve elements are adapted to engage so that the large forces exerted on the implanted device by reason of the knee's function and mechanics are distributed over the substantial area of the congruent thrust bearing surfaces. Non-hinged knee joints with congruent bearing surfaces which allow flexion and tibial rotation are shown as alternate constructions.

35 Claims, 10 Drawing Figures

PROSTHETIC KNEE JOINT

BACKGROUND OF THE INVENTION

This application is a continuation-in-part of application Ser. No. 605,208 filed on Aug. 15, 1975, now abandoned.

The present invention relates to prosthetic joints, and more particularly to prosthetic joints used for total human knee joint replacement and which permit the knee joint to perform in an almost natural anatomical manner.

Medically, hinged knee joints are implanted when the tissues of the knee joint are grossly deteriorated from disease or other cause, particularly the loss of function of the four major ligaments of the knee: 2 cruciate ligaments and 2 collateral ligaments.

In the normal anatomical function of the healthy knee, the geometry of motion is complex. The knee is essentially a large knuckle joint, in fact, it is the largest joint in the body. The upper surface of the tibia provides two bearing surfaces which are essentially flat and essentially at right angles to the axis of the shaft of the tibia. The co-acting lower end of the femur consists of two large rounded ends called condyles. The condyles roll and slide on the two supporting surfaces of the tibia, called the tibial plateau. There is no congruency or symmetry in either joint between the two corresponding surfaces on the tibia and the two corresponding condyles. Normally, bone joint surface pressure loadings are disbursed favorably through cartilage covered articular surfaces, and the menisci and synovium contribute to adequate normal function. The two rolling and sliding actions, plus the result of forces and constraints put on the knee joint by muscles, ligaments, joint capsule, etc. result in a relative axial rotation between the two cooperating bones, the femur and the tibia in addition to the basic motion of flexion. If one sits with the leg fully extended in front of him, as he flexes the knee downward through 90 degrees, the tibia rotates inwardly, approximately 10 degrees. This axial rotation of the tibia is relatively small and not at all uniform per unit of flexion occurring mostly in the initial phases of flexion from the leg being fully extended. In general, hinge-type prosthetic joints do not incorporate this relative axial rotation and therefore do not closely simulate the natural action of the knee joint.

Furthermore, hinge type prosthetic knee joints have two problems associated with permanent anchorage in the bone. One, they are restrained against axial rotation of the tibia. This axial rigidity causes torque shock loads applied to the lower limb or foot to be resisted by the prosthetic fastening to the bone. Such fastening is most commonly achieved by use of a quick setting bone cement like polymethyl methacrylate, which materials do not well resist such shock loads. Two, a knee joint fitted with a hinge prosthesis has a limited range of flexion of perhaps 90° to 120°. If such a restored joint is subject to attempted flexing beyond its limit, the bending force can act on the bones to cause them to separate or distract. This occurrence can cause the hinge prosthesis to pull out of its cement bed. Therefore, these two factors can cause hinge type prostheses to come loose from their original implanted condition, which is a relatively frequent cause of failure for this type of prosthesis.

To reproduce a natural leg movement to the maximum possible extent, a prosthetic knee joint must provide two degrees of freedom, namely, bending or rotation of the tibia about an axis transverse to the shaft of the femur, which motion is called flexion, and rotation of the shaft of the tibia about its axis relative to the axis of the shaft of the femur. Furthermore, the prosthetic knee must accommodate the large stresses placed on the bearing surfaces of the prosthesis. These stresses can cause inadequate bearing surfaces to wear out. Obviously, wear of the bearing surfaces is undesirable, because movement of the prosthetic knee would be impaired and the debris resulting from wear would be harmful to the body.

To date, knee prostheses either do not provide rotation in more than one plane, or have bearing surfaces which tend to wear away. The development of a prosthetic joint involves a conundrum in that the greater the degree of success of the operative procedure, the more likely the chance of failure of the prosthesis. The preceding stems from the fact that the patient candidate for the prosthetic joint has impaired joint function and therefore limited mobility. If the implantation of an artificial joint reduces pain and improves mobility, the patient becomes more active. The greater the degree of improvement of joint function, the greater the probability of increased activity by the patient. Increased activity will be accompanied by increased load and motion on the joint, which combine to tend to cause mechanical failure of the artificial joint. This condition is particularly pronounced in the knee because of the complex geometry of motion and the large load forces involved.

To illustrate the magnitude of the forces acting within the knee joint, it is possible for a 200 lb. man in a half squat on one leg to impose a compressive load of about 900 lbs. at the joint surface between the femur and the tibia. This load is due only to static conditions. Dynamic loads can be significantly larger.

Considering only those prostheses permitting rotation in two planes, prostheses can be divided into at least three general classes.

A first class includes those knee prostheses in the form of inserts or modules, or resurfacing devices which replace the bicondylar joint of a human limb and are constructed to simulate the shape of that bicondylar joint. These prostheses attempt to imitate the natural motion of a joint by structuring the surfaces of the joint to imitate nature. However, these joints have high local loading stresses at selective points on the bearing surfaces and therefore tend to wear away at these selective points, thus resulting in degradation and ultimate failure of the prosthetic joint. As a result, such prostheses may have to be replaced after only a short period of use, depending of course on the degree of activity of the patient.

A second class of prostheses includes a ball and socket joint with means to limit motion to rotation in two planes. In such a joint, the means to prevent rotation in the third plane is commonly constructed so that unit bearing loads are high, and early bearing failure generally result when patient activity increases.

A third class of prostheses comprises a fixation stem implantable in a tibia and having an upstanding arm extending from the top of the fixation stem. The top of the upstanding arm may be in the form of a ball. The ball fits into a socket in the space between the condyloid members of the femoral prosthesis. In this construction, the condyloid prosthetic members of the prosthesis of the femur rotate and slide on the prosthetic surfaces of the tibia. This relative motion between the non-congruent prosthetic surfaces under the high bearing loads imposed by the function of the joint may lead to premature mechanical failure of the prosthetic bearing surfaces.

The preferred embodiment of the present invention overcomes the above-discussed disadvantages of the known art by providing a prosthetic joint in which the bones can undergo rotation in two planes, yet will not be subject to excessive unit bearing stresses. Bearing surfaces are arranged to be in contact over large areas of engagement so that the large forces exerted by reason of the function and mechanics of the knee are spread out over the entire area of the engagement. Mated bearing surfaces are of large area and are of congruent geometry. Therefore, local stresses (force per unit area) are reduced from those values found in the prior art wherein the bearing surfaces are not congruent. With the arrangement of the present invention, the prosthetic device will continue to function with a minimum of wear and simulate normal action of a human limb for long periods of time under conditions of normal patient activity.

The preferred embodiment substantially eliminates the transmission of shock torque loads through the prosthesis by virtue of allowing relative axial rotation between the bones. Such torque loads are transmitted through tendons, ligaments and other soft tissues covering the joint. In addition, this embodiment has no fixed coupling between the two bones and is designed to extend or distract should flexion beyond approximately 120° cause the bones to move apart or move axially with respect to each other. Accordingly, the present invention overcomes the two principal factors contributing to loosening of hinge type prostheses.

Further, the preferred embodiment provides the very practical advantage of allowing the surgeon improved access to the posterior joint space during the surgical procedure.

One alternate form of the prosthesis includes a tibia stem component which is implantable directly in the tibia and which stem upper surface supports a bearing shoe. The bearing shoe is axially rotatable relative to the tibia and is confined by guide elements at the edge of the upper surface of the tibia stem component. This embodiment can be designed to allow the cruciate ligaments to remain intact. In this embodiment, the femoral and tibial components are not hingedly coupled.

A second alternate is similar to the above, and permits removal of a minimum of bone from the tibia.

Accordingly, it is an object of the present invention to provide a durable prosthetic joint which enables the limb to undergo approximate natural movement.

It is another object of the present invention to enable a pair of human bones joined by a prosthetic joint to undergo relative rotation in at least two planes and thereby closely simulate the natural action of the joint.

It is yet another object of the present invention to provide a prosthetic device having an improved bearing configuration.

SUMMARY OF THE INVENTION

A prosthetic device embodying the present invention includes a fixation means adapted to be attached to the femur bone and a coupling means positioned at one end of the fixation means. The coupling means may be similar to the hinged coupling means of the prosthetic device disclosed in application Ser. No. 554,144 filed on Feb. 28, 1975, now U.S. Pat. No. 3,996,624, issued Dec. 14, 1976, incorporated herein by reference. The coupling means is pivotally attached to a flanged stem element which has a rod depending thereon. A flanged sleeve element is adapted to be implanted in a tibia bone and receives the depending rod and flange of the stem element in a manner which permits relative rotation between the stem and the sleeve and distraction or separation of the stem from the sleeve. The stem element and the sleeve each have cylindrical and planar bearing surfaces which are engaged when the stem rod is received in the sleeve. The two mating bearing surfaces are respectively large and congruent, therefore forces exerted on the device are distributed uniformly, thereby reducing unit loading stresses placed on the bearing surfaces. Stop elements mounted on the flange of the sleeve bearing surface are shaped to correspond to the shape of the flange element of the stem element. The stem flange and the stop elements cooperate to limit the amount of relative rotation (axial to the shaft of the tibia) between the femur and the tibia.

Therefore, the device of the present invention enables a human limb to approximate normal movements comprising rotation in two planes while distributing load forces over substantial bearing areas. By permitting rotation in two planes while reducing local unit stresses placed on the bearing elements, the device embodying the present invention minimizes wear and maintains improved prosthetic motion of a limb over long periods of time.

For a better understanding of the present invention, together with other details and features thereof, reference is made to the following description taken in conjunction with the accompanying drawings.

DESCRIPTION OF THE PREFERRED EMBODIMENTS

Figures 1, 2, 5, 6:
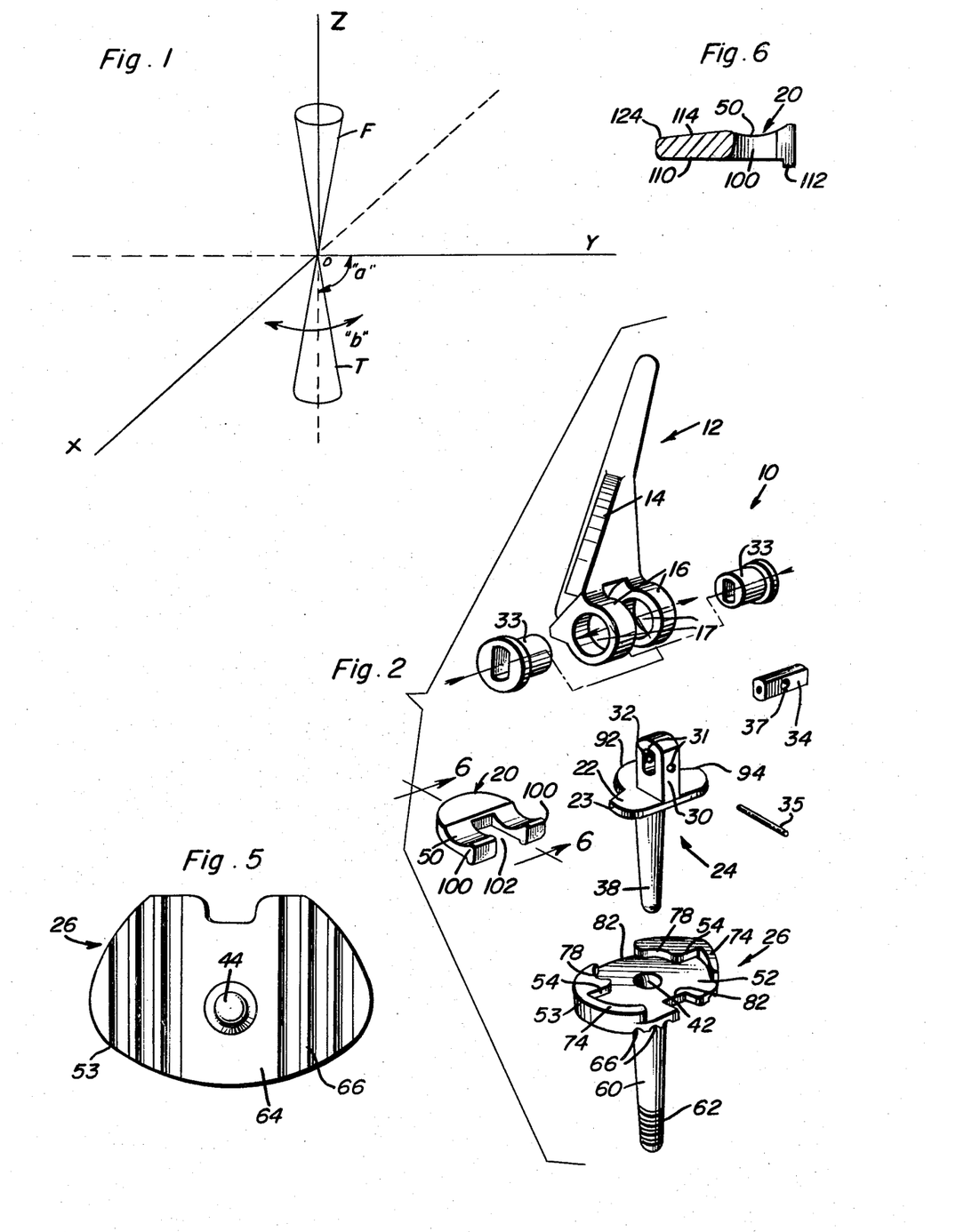
FIG. 1 is a diagram showing the kinematics of a prosthetic joint embodying the teachings of the present invention.
FIG. 2 is an exploded perspective of a prosthetic joint embodying the teachings of the present invention.
FIG. 5 shows the underneath side of the tibia sleeve.
FIG. 6 shows a bearing shoe adapted for use with the prosthetic joint of the present invention.

FIG. 1 shows the kinematics of the prosthesis embodying the present invention. As illustrated schematically in FIG. 1, in the extended position of the leg or lower limb, the femur "F" and the tibia "T" are generally aligned in an essentially continuous line along the z-axis of the co-ordinate system shown in FIG. 1. As used herein, "transverse rotation" means flexion and refers to rotation of the tibia about the x-axis transverse thereto and occurs in the y-z plane, and "axial rotation" refers to rotation of the tibia about its longitudinal (z) axis. Thus, in FIG. 1, flexion is represented by arrow "a" and axial rotation is represented by arrow "b". As the tibia of a natural knee is flexed through 90 degrees from the fully extended knee position shown in FIG. 1, it undergoes a rotation about its longitudinal axis of approximately 10 degrees. The prosthesis embodying the present invention enables the tibia to execute the aforementioned axial rotation while the tibia executes the transverse rotation.

FIG. 2 shows an exploded perspective of a prosthesis 10 embodying the present invention. Prosthesis 10 comprises a femoral, or first component 12 having a fixation shank 14 adapted to be implanted in femur "F" and a pair of spaced apart bearing elements 16, which simulate the condyloid elements of a natural knee, each of which has holes 17 therethrough, said holes 17 defining a bearing surface. Each of holes 17 contains a sleeve element 33. Bearing elements 16 comprise a convex surface of revolution having an axis approximately perpendicular to the axis of the femur, and are adapted to be seated in, and bear upon, a bearing shoe 20 which has concave upper surfaces 50 and which is adapted to be seated on a plateau surface 22 of flange portion 23 of tibia stem 24. The bearing shoe 20 and the tibia stem 24 are sometimes collectively referred to herein as the intermediate, or second, component. The bearing surfaces 16 and the bearing surfaces defining the holes 17 are concentric and part of the same unitary mechanical element and are adapted to support weight and be subject to force while experiencing movement. Upper part 30 of tibial stem 24 is attached at one end to plateau 22 and defines a hole 32 therethrough near the other end together with holes 31 which exit transverse to hole 32. A transverse support shaft 34 provided with a transverse hole 37 fits through hole 32 and sleeve elements 33 to attach femoral component 12 to tibia stem 24. Pin 35 is inserted through holes 31 and 37 to retain shaft 34. It is here noted that the coupling means and bearing elements of the present invention includes the elements which attach the femoral component to the tibia stem, and a coupling means suitable for use with the present prosthetic joint is fully disclosed in the aforementioned U.S. Pat. No. 3,996,624. A lower rod 38 depends from the lower surface of the flange portion 23 and is received in a hole 42 of a tibia sleeve 26 in a manner which permits free rotation of the tibia stem within the sleeve about the longitudinal axis of the rod. The tibia sleeve, or third component 26 is adapted to be implanted in a tibia. Furthermore, tibia sleeve 26 has an upper thrust bearing surface 52 on a flange portion 53 which is adapted to engage a thrust bearing surface 40 located on the lower surface of the stem flange portion 23.

Because the knee is subject to large compressive loads which manifest themselves as thrust forces acting parallel to the axis of rod 38, the cooperating thrust bearing surfaces 40 and 52 are made generously large. Thus, the bearing load per unit area is made sufficiently low to provide long bearing life with low wear rate. The interface of surfaces 40 and 52 is shown as being flat or planar. However, any relatively shallow surface of revolution whose axis is approximately parallel to the axis of the tibia such as a cone, part of a sphere or other configuration with equivalent projected bearing area to the flat interface can be used to define the congruent thrust bearing interface between flange 23 of stem 24 and surface 52 of sleeve 26 so long as the congruent thrust bearing surfaces forming the interface are able to function as a low friction thrust bearing capable of freely rotating under the full range of loads that the knee experiences. It is known, for example, that conical mating metal surfaces where the apex angle of the cone is less than 15° will either lock when subjected to axial thrust load, or the interface friction will increase to such an extent as to become wholly impractical in a knee joint. Therefore, it is necessary that the conical mating surfaces have an apex angle sufficiently great to permit low friction axial rotation while subjected to axial thrust load. It is mandatory, therefore, that the conical apex angle be greater than 15°, and preferably greater than 30°. As a practical design matter, it is necessary in order to achieve the best results that an apex angle greater than 120° be used. A flat surface (i.e., a conical apex angle of 180°) is being used commercially with excellent results.

Whereas the above discussion considers a conical bearing surface by way of example only, it should be appreciated that other surface of revolution configurations can be employed in the invention. The mean curvature of such other surfaces of revolution or the defined apex angle of such other surfaces of revolution must meet the above criteria, i.e., must be shallower than or greater than, respectively, an approximate designated apex angle of an approximately similar conical surface of revolution, the smallest angle being 15° for the reasons explained, 30° being the preferable lower limit, and 120° being the practical design limitation.

To permit the artificial joint to distract under conditions which may exist at the limit of maximum flexion, the stem 24 is free to move out of sleeve 26. Thrust bearing surfaces 40 and 52 are free to separate one from the other. Rod 38 is free to slide upward in hole 42. The maximum separation anticipated in use is estimated to be one half inch. Rod 38 serves to impart guidance and lateral stability of stem 24 relative to the sleeve 26. In order to maintain stability of alignment to insure proper re-engagement when coming together the rod 38 should be at least 1.5 inches long. Rod 38 and hole 42 can be straight or tapered, so long as there is clearance between them when fully engaged. Because the created implant cavity and the tibia bone T are tapered with the largest dimension nearer the joint, it is structurally advantageous to make rod 38, hole 42, and sleeve 44 tapered as shown in the drawings.

While the feature of the tibia stem 24 as being freely movable axially in tibia sleeve 26 is based on allowing the artificial joint to be extensible for functional reasons, it provides another very practical advantage. This advantage presents itself during the surgical implant procedure for the following reasons. In conventional hinged knee prostheses, there are generally two main components to the prosthetic joint: the femoral component and the tibial component. Immediately after these components are fixed to the bone by cementing, the access to the posterior joint space is blocked by the presence of the two components. The surgical opening is at the anterior of the knee and yet excess cement must be removed from behind the prosthesis where vision is often blocked and access is limited. There can also be stray bone chips and occasionally even fixed parts of the bone which interfere with the free function of the hinge. In the case of the inventive prosthesis, the femoral component 12 is cemented in place and the tibia sleeve 26 is cemented in place, subsequently the tibial stem 24 can be inserted and removed repeatedly at the will of the surgeon while he tries the function of the joint and examines the posterior joint space with clear view and access. The surgeon can therefore be certain that there are no extraneous pieces of cement or bone in the joint space and that the joint flexes freely through the entire desired range of motion. This very practical consideration is of importance to the surgeon.

Figure 3:
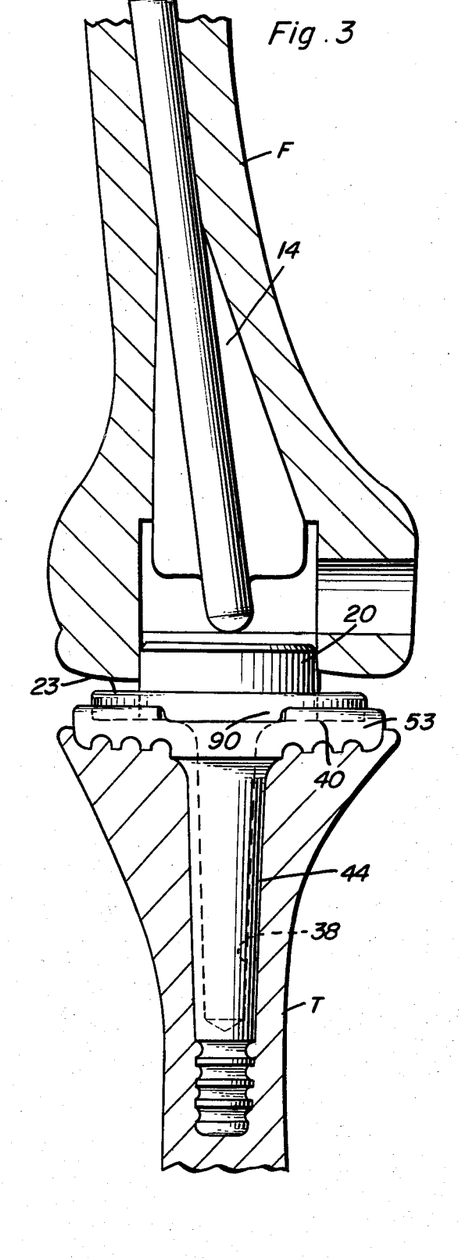
FIGS. 3 and 4 show two views of the prosthetic joint joining a pair of bones.
Figure 4:
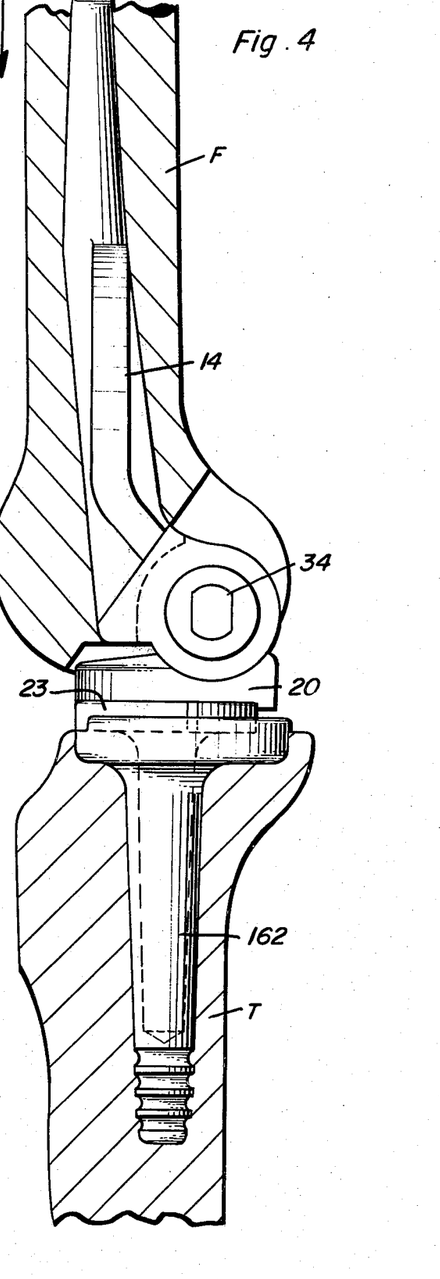

The bearing surface 52 has stops 54 which correspond to the shape of the flange portion 23 and coact with corresponding wing elements 94 formed on the flange portion 23. The coupling means permits flexion of the tibia with respect to the femur, and the tibia stem 24 undergoes axial rotation relative to the tibia sleeve 26 which is fixed in the tibia "T". Therefore the femur "F" and tibia "T" are premitted to rotate in two planes with respect to each other. The axial rotation is limited by stops 54 and wing elements 94. FIGS. 3 and 4 show the assembled prosthesis 10 installed in the femur "F" and tibia "T" to form the prosthetic knee joint of the invention.

With reference to FIGS. 2, 3, 4 and 5, tibia sleeve 26 is shown as comprising a portion 60 depending from flange portion 53 having grooves 62 on the end thereof which is remote from the head portion. Portion 60 is adapted to be cemented into the medullary canal of the tibia and the grooves 62 ensure a secure connection between the sleeve and the tibia. Likewise, lower surface 64 of flange portion 53 has a plurality of grooves 66 herein for ensuring a secure connection between the flange portion 53 and the upper bearing surfaces of the tibia.

As shown in FIG. 2, depending portion 60 is tapered and has a cross-section adjacent grooves 62 which is smaller than the cross-section thereof adjacent the flange portion 53. The taper of approximately 2 degrees per side is preferred by reason of the taper in the tibia bone.

As shown in FIG. 2, flange portion 53 of tibia component 26 is essentially oval-shaped, and the stops 54 are positioned on the marginal edges thereof. The stops 53 extend radially inward from the marginal edge of the sleeve flange portion 53. Ribs 74 are defined on the periphery of flange portion 53 and have a shape which conforms to the generally arcuate shape of the flange portion outer periphery. The stops 54 are defined by surfaces which join with ribs 74 on one side and concave surfaces 78 on the other side. The flange portion 53 is recessed at 82 to provide a slot to accommodate blood vessels and the like. The hole 42 may be offset from the center of the flange portion 53.

The grooves 66 in flange portion 53 may be essentially parallel to each other, or any other suitable configuration.

The tibia stem 24 is shown in FIGS. 2, 3, 4 and includes tapered rod 38 which moves freely in the taper of the hole 42 in tibia sleeve 26. Fillets 90 at the juncture of lower rod 38 and the surface 40 are shaped to reduce stress concentrations.

The perimeter of flange portion 23 is shown in FIG. 2 as having a circular sector 92 which fits within the concave surfaces 78. The circular sector 92 on each end joins abutment shoulders 94 which intersect the circular sector 92 at appropriate points to permit a limited degree of relative rotation of the tibia sleeve 26 about its longitudinal axis with respect to the stem 24 before one of the shoulders 94 abuts a corresponding shoulder 54. Therefore, this angle is chosen to correspond to the desired amount of rotation of a tibia about its longitudinal axis relative to the femur. The angle therefore is preferably in the order of 20 degrees in each direction, however, other extents of rotation are possible depending upon specific circumstances. Ultimate practical experience may show that in some cases the amount of rotation need not be limited by the prosthesis. That is, the patient's anatomy remaining outside the prosthesis, tendons, ligaments and scar tissue may provide enough restraint to rotation. As both shoulders 94 are displaced from shoulders 54 when the tibia sleeve 26 is in the repose or neutral position, the tibia sleeve 26 can rotate about its longitudinal axis in either a clockwise or a counterclockwise direction.

Bearing shoe 20 is shown in FIGS. 2, 3, 4 and 6, and is seen to be U-shaped having a pair of legs 100 and a central slot 102 having a cross-section which corresponds to the transverse cross-section of upstanding post 30. The bearing shoe is adapted to be seated on the surface 22 and be engaged by bearing elements 16. As shown in FIG. 6, the shoe defines lips 112 on its lower surface 110 which depend from each of the legs 100. Each lip is adapted to engage an edge of the stem flange portion 23 as is shown in FIG. 4, when the shoe is seated on surface 22.

As shown in FIG. 6, the shoe has an upper surface 114 which is divided into two sections, a concave section formed by surfaces 50 and a tapered section 124. When the shoe is positioned in the prosthesis 10, each of the arcuate surfaces 50 is adapted to receive one of the bearing elements 16. When assembled and implanted, the bearing elements 16 are adapted to be in weight bearing relationship with the bearing shoe 20 which has concave upper surfaces 50. See U.S. Pat. No. 3,996,624 for a description of the advantageously large bearing area of the hinge joint provided by redundant bearings 16 in 50 and 33 in 17.

With reference to the figures, the compressive force on the prosthesis generated by the function and mechanics of the knee is distributed over the relatively large surface area of the thrust bearing surfaces 40 and 52. Thus, these surfaces will not wear as rapidly as would surfaces with smaller areas of contact. Therefore, the device embodying the present invention permits rotation in two planes while having adequate bearing configurations to ensure a long lasting prosthesis. The bearing surfaces 40 and 52 are adapted to distribute weight and transmit force uniformly while at the same time able to undergo relative rotation.

The elements of the prosthesis 10 must be fabricated from biologically compatible, surgically implantable materials. For example, the tibia sleeve 26, the bearing shoe 20, and a sleeve elements 33 can be a plastic, such as ultrahigh molecular weight polyethylene, and the remaining elements are preferable of surgically implantable structural metal. The femoral component and the tibia stem can both be of grade 316 surgical stainless steel, or they can both be of an acceptable cast chromium, molybdenum, cobalt alloy (such as ASTM F75-74) or the femoral component can be of cast chromium, molybdenum, cobalt alloy while the tibial stem can be of titanium-6 aluminum-4 vanadium alloy.

The device of the present invention is adaptable to various sizes and either a right or left leg.

Figure 9:
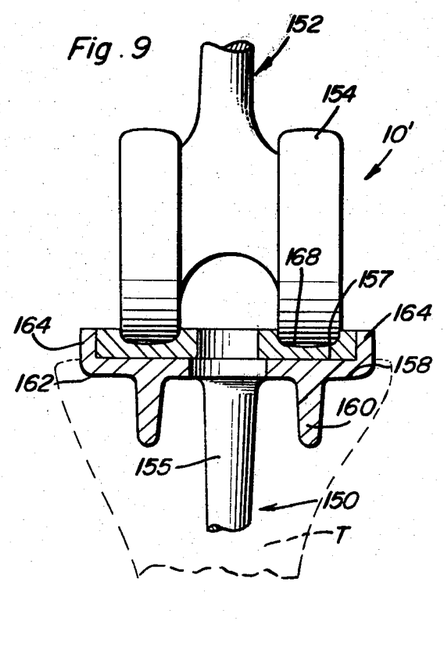
FIGS. 9 and 10 show another alternative form of a prosthesis according to the teachings of the present invention.
Figure 10:
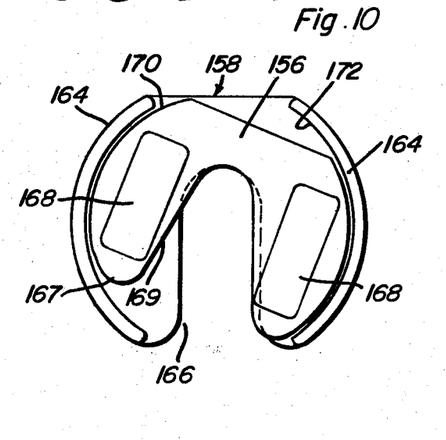

FIGS. 9 and 10 show an alternative form of the prosthesis which includes a prosthesis 10' comprising a tibial component 150 implanted directly in a tibia "T", a femoral component 152 having condyloid elements 154, and an intermediate bearing shoe 156 seated on surface 157 of head 158 of the tibial element. The condyloid components 154 engage seats 168 in the shoe 156. The tibial component 150 comprises a rod 155 and projection elements 160 depending from surface 162 of the head 158, all of which can be attached to the upper end of the tibia to secure the tibial components 150 thereto. Bearing shoe 156 is to a degree similar to the bearing shoe 20 of the preferred embodiment. Head 158 comprises a pair of guide elements 164 located on the marginal edge thereof and a slot 166 in which the knee cruciate ligaments are located. Bearing shoe 156 is U-shaped and comprises a pair of legs 167, each having bearing element seats 168. A slot 169 in the shoe 156 corresponds to the slot 166 of the tibial component head 158. The outer surface 170 of the bearing shoe 156 and the inner surface 172 of the guide elements 164 are curved along similar radii and cooperate to guide the rotation of the tibia with respect to the longitudinal axis of tibia. Condyloid elements 154 are preferably surfaces of revolution as are bearing element seats 168, and each element 154 has a contour which is congruent to the seat 168 in which it moves. This geometry provides adequate bearing area for the motion of flexion. Axial rotation of the tibia is permitted by the rotation of bearing shoe 156 on the weight bearing or thrust bearing surface 157 of tibial component 150. This interface is between congruent bearing surfaces of generous area. The tibial component rod 155 is shown offset from the center of the head, however, other suitable positions for these elements can be selected.

FIG. 10 depicts a space between the outer surface 170 of the bearing shoe 156 and the inner surface 172 of the guide elements 164. This space may be so proportioned as to allow bearing shoe 156 to move in a transverse forward and rearward direction that may result due to the action of the cruciate ligaments. As a consequence, the bearing shoe 156 is adapted to move forward and backward, as well as rotationally, relative to the head 158.

The prosthesis of FIGS. 9 and 10 differs from the preferred embodiment in that for stability it relies, to a large extent, on functioning knee joint ligaments. That is, it is adapted to implantation in patients with a lesser degree of degradation of the knee joint than is the preferred embodiment. The same is true for the prosthesis shown in FIGS. 7 and 8.

Figure 7:
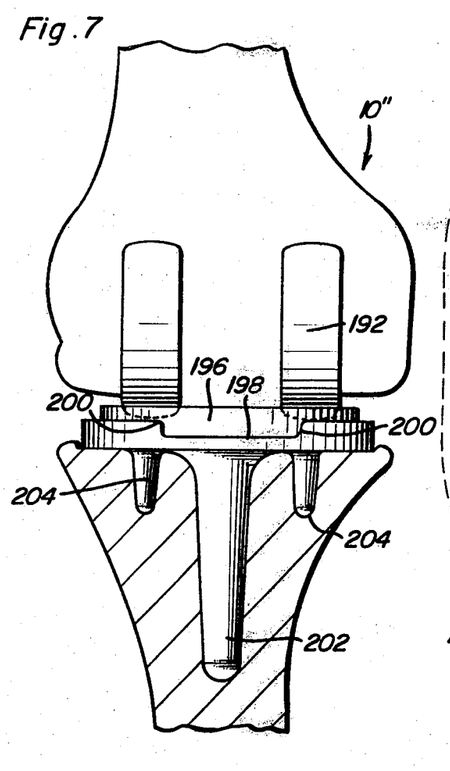
FIGS. 7 and 8 show an alternative form of the present invention.
Figure 8:
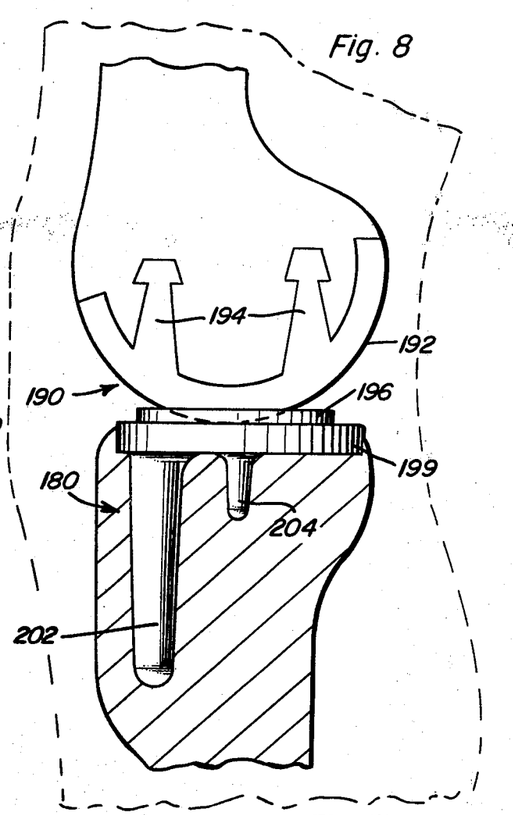

FIGS. 7 and 8 show still another embodiment of the prosthesis embodying the present invention. The prosthesis 10″ comprises a tibial component 180 similar to the tibial component 150, and a femoral component 190. The femoral component 190 comprises a pair of arcuate bearing elements 192 attachable to the lower end of a femur by suitable means, such as upstanding stems 194 which are implanted in the femur using polymethyl methacrylate cement. The tibial component 180 supports a bearing shoe 196 which engages with the bearing elements 192. The bearing shoe 196 is seated on the upper surface 198 of tibia head 199 of the tibial component 180. The function of bearing shoe 196 is similar to that described for the shoe 156, and is guided by ribs 200 formed on the periphery of head 199. Stems 202 and 204 provide a means to attach the tibial component 180 to the tibia.

The prosthesis 10″ has the advantage of being implantable while requiring the removal of minimal amount of bone.

In the parent application, a means for locking was disclosed for setting the axial alignment of the femur and tibia. It has been found in practice, however, that such locking means is unnecessary, and hence the locking means feature is not disclosed herein.

Obviously, numerous modifications and variations of the present invention are possible in light of the above teachings. It is therefore understood that, within the scope of the appended claims, the invention may be practiced otherwise than as specifically described.

What is claimed is:

1. A prosthetic device for forming a joint between a pair of human or animal bones comprising:
    first fixation means adapted for attachment to one of the bones;
    first bearing surface on said first fixation means, which said first bearing surface is a convex surface of revolution whose axis is approximately perpendicular to the axis of said one of the bones;
    second fixation means adapted for attachment to the other bone;
    second bearing surface on said second fixation means, which said second bearing surface is a surface of revolution whose axis is approximately parallel to the axis of said other bone;
    a bearing element concave on one side interposed between said first bearing convex surface and said second bearing surface, wherein said bearing element on the concave side mates in congruent bearing relationship with said first bearing convex surface, and on the opposite side mates in congruent bearing relationship with said second bearing surface; and
    said bearing element in said congruent bearing relationship with said second bearing surface being freely rotatable in a plane approximately perpendicular to the axis of the said other bone while transmitting force to said second bearing surface.

2. A prosthetic device as claimed in claim 1 wherein the second mentioned congruent bearing relationship is defined by surfaces of revolution defining an apex angle greater than an approximate 30° apex angle of an approximately similar conical surface of revolution.

3. A prosthetic device as claimed in claim 1 wherein the second mentioned congruent bearing relationship is defined by surfaces of revolution defining an apex angle greater than an approximate 120° apex angle of an approximately similar conical surface of revolution.

4. A prosthetic device as claimed in claim 1 wherein said second bearing surface is a substantially flat surface substantially perpendicular to the axis of said other bone.

5. A prosthetic device as claimed in claim 1 wherein said second bearing surface is a nearly flat surface of revolution whose axis is approximately parallel to the axis of said other bone.

6. A prosthetic device as claimed in claim 1 further including stop means for limiting the movement of said bearing element in said plane.

7. A prosthetic device as claimed in claim 1, wherein said bearing element is freely movable in transverse and rotary directions in said plane approximately perpendicular to the axis of the said other bone.

8. A prosthetic device as claimed in claim 1, wherein said bearing element is free of any hinged connection with said first fixation means.

9. A prosthetic device as claimed in claim 1, wherein said bearing element comprises a pair of legs.

10. A prosthetic device as claimed in claim 1, wherein said second bearing surface includes a slot means for accommodating cruciate ligaments.

11. A prosthetic device as claimed in claim 1, wherein said first bearing surface comprises a pair of arcuate bearing elements, and said first fixation means comprises a pair of stems, each stem connected to a separate arcuate bearing element, wherein each stem is capable of implantation in said one of the bones.

12. A prosthetic device for forming a joint between a pair of human or animal bones comprising:
   first fixation means adapted for attachment to one of the bones;
   first bearing surface on said first fixation means, which said first bearing surface is a convex surface of revolution whose axis is aproximately perpendicular to the axis of said one of the bones;
   second fixation means adapted for attachment to the other bone;
   second bearing surface on said second fixation means, which said second bearing surface is a surface of revolution whose axis is approximately parallel to the axis of said other bone;
   a bearing element concave on one side interposed between said first bearing convex surface and said second bearing surface, wherein said bearing element on the concave side mates in congruent bearing relationship with said first bearing convex surface, and on the opposite side mates in congruent bearing relationship with said second bearing surface;
   said bearing element in said congruent bearing relationship with said second bearing surface freely rotatable in a plane approximately perpendicular to the axis of the said other bone while distributing weight and transmitting forces to said second bearing surface; and
   said second mentioned congruent bearing relationship being defined by surfaces of revolution defining an apex angle greater than an apex angle of an approximately similar conical surface of revolution of sufficient magnitude to enable free mobility.

13. A prosthetic device as claimed in claim 12 wherein the magnitude of said apex angle is greater than 30°.

14. A prosthetic device as claimed in claim 12 wherein the magnitude of said apex angle is greater than 120°.

15. A prosthetic device for forming a joint between a pair of human or animal bones comprising:
   first fixation means adapted for attachment to one of the bones;
   first bearing means mounted on said first fixation means;
   second fixation means adapted for attachment to the other bone, and comprising a bearing surface means for supporting weight and being subjected to force;
   a unitary intermediate load bearing member having two surfaces, one surface comprising a thrust bearing surface means for matingly engaging said bearing surface means, and adapted to distribute weight and to transmit forces while rotating freely relative to said bearing surface means independent of the position of the first bearing means, the other surface of said intermediate load bearing member comprising means for supporting said first bearing means and adapted to support weight and be subjected to force from said first bearing means while experiencing relative motion with said first bearing means.

16. A prosthetic device as claimed in claim 15, wherein said intermediate load bearing member comprises two elements positioned in back-to-back relationship, and wherein said one surface is associated with one element and said other surface is associated with the other element.

17. A prosthetic device for forming a joint between a pair of human or animal bones comprising:
   first fixation means adapted for attachment to one of the bones;
   first bearing means mounted on said first fixation means;
   second fixation means adapted for attachment to the other bone, and comprising a bearing surface means for supporting weight and being subjected to force;
   a unitary intermediate load bearing member having two surfaces, one surface comprising a thrust bearing surface means for matingly engaging said bearing surface means, and adapted to distribute weight and to transmit forces while rotating freely relative to said bearing surface means, wherein said bearing surface means comprises an arcuate flange portion along its periphery and stop means extending from the arcuate flange portion radially inward, and wherein said thrust bearing surface means of said intermediate load bearing member comprises abutment means for engaging said stop means, and wherein the other surface of said intermediate load bearing member comprises means for supporting said first bearing means and adapted to support weight and be subjected to force from said first bearing means while experiencing relative motion with said first bearing means.

18. A prosthetic device as claimed in claim 17, wherein said second fixation means comprises a sleeve means for receiving a rod, said sleeve means adapted to be fixedly connected to said other bone, said sleeve means extending from a hole defined in said bearing surface means, and wherein said intermediate load bearing member comprises a rod extending from said thrust bearing surface means and substantially perpendicular thereto, said rod adapted to be positioned within said sleeve and rotatable therein.

19. A prosthetic device as claimed in claim 18 wherein said rod is axially movable within said sleeve.

20. A prosthetic device for joining a pair of human or animal bones comprising:
   a first prosthesis having a condylar portion and a fixation portion, said condylar portion including two laterally spaced apart condyloid elements each having a first bearing surface defined by the outer periphery of said element and a second bearing surface defined by an opening in said element adapted to receive a transverse support shaft, said fixation portion being adapted to be fixed to one of said bones, said first and second bearing surfaces being concentric and part of the same unitary mechanical element and being adapted to support weight or be subjected to force while experiencing relative motion;
   a second prosthesis having a bearing surface means for supporting weight and being subjected to force and a fixation portion being adapted to be fixed to the other one of said bones;
   an intermediate load bearing member having two surfaces, one surface comprising a thrust bearing surface means for matingly engaging said bearing surface means and adapted to distribute weight and to transmit forces and to rotate relative to said bearing surface means, the other surface of said intermediate load bearing member having a weight-bearing portion, said weight-bearing portion including mating bearing surfaces against which said first prosthesis bear, a center portion fitted between the condyloid elements of said first prosthesis, said center portion having an opening adapted to receive a transverse support shaft;

a transverse support shaft having a central portion positioned in said opening in said center portion of said load bearing member and end portions received in said openings in said condyloid elements in said first prosthesis, said shaft being non-rotatably mounted relative to said load bearing member, said end portions of said shaft being adapted to rotate in said openings in said condyloid elements while bearing against said second bearing surface; and said mating engagement between said thrust bearing surface means and said bearing surface means is defined by surface of revolution defining an apex angle greater than an apex angle of an approximately similar conical surface of revolution of sufficient magnitude to enable free mobility.

21. A prosthetic device as claimed in claim 20 wherein the magnitude of said apex angle is greater than 30°.

22. The prosthetic device as claimed in claim 20 wherein the magnitude of said apex angle is greater than 120°.

23. A prosthetic device for forming a joint between a pair of human or animal bones comprising:

first fixation means adapted for attachment to one of the bones;

a second fixation means adapted for attachment to the other bones;

an intermediate member, means for coupling said intermediate member with said first fixation means for forming a hinge whose axis of rotation is approximately perpendicular to the axis of the said one bone; and said intermediate member mating with said second fixation means such that said intermediate member and said second fixation means bear on one another at a mutually congruent thrust bearing surface of revolution for permitting rotational motion between said intermediate member and said second fixation means while force is transmitted therebetween, and permitting axial motion of said intermediate member relative to said second fixation means, where the axis for said rotational and axial motion is approximately parallel to the axis of said other bone.

24. A prosthetic device as claimed in claim 23 wherein said intermediate member in said congruent thrust bearing relationship with said second fixation means is freely movable in a plane approximately perpendicular to the axis of the said other bone while transmitting force to said second fixation means.

25. A prosthetic device as claimed in claim 24 wherein said second fixation means comprises a sleeve means for receiving a rod, said sleeve means adapted to be fixedly connected to said other bone, said sleeve means extending from a hole defined in said thrust bearing surface, and wherein said intermediate member comprises a rod extending from said mutually congruent thrust bearing surface and substantially perpendicular thereto, said rod adapted to be positioned within said sleeve and rotatable therein.

26. A prosthetic device as claimed in claim 24 wherein said congruent thrust bearing relationship is defined by surfaces of revolution defining an apex angle greater than an apex angle of an approximately similar conical surface of revolution of sufficient magnitude to enable free mobility.

27. A prosthetic device as claimed in claim 26 wherein the magnitude of said apex angle is greater than 30°.

28. A prosthetic device as claimed in claim 26 wherein the magnitude of said apex angle is greater than 120°.

29. A prosthetic device as claimed in claim 26 wherein said mutually congruent thrust bearing surface is substantially flat.

30. A prosthetic device as claimed in claim 26 wherein said mutually congruent thrust bearing surface is a nearly flat surface of revolution whose axis is approximately parallel to the axis of said other bone.

31. A prosthetic device as claimed in claim 25 further including stop means for limiting the movement of said congruent thrust bearing.

32. A prosthetic device as claimed in claim 31 wherein said stop means limits movement of said congruent thrust bearing to approximately 40 degrees.

33. A prosthetic device as claimed in claim 31, wherein said second fixation means comprises an arcuate flange portion along its periphery and stop means extending from the arcuate flange portion radially inward, and wherein said congruent thrust bearing surface of said intermediate load bearing member comprises abutment means for engaging said stop means.

34. A prosthetic device for joining a pair of human or animal bones comprising:

a first prosthesis having a hinge portion and a fixation portion, said hinge portion including two laterally spaced apart bearing elements each having a bearing surface defined by an opening in each of said elements adapted to receive a transverse support shaft, said fixation portion being adapted to be fixed to one of said bones, said bearing surface being adapted to support weight or be subjected to force while experiencing relative motion;

a second prosthesis having a bearing surface means for supporting weight and being subjected to force and a fixation portion being adapted to be fixed to the other one of said bones;

an intermediate load bearing member having a thrust bearing surface means for matingly engaging said bearing surface means and adapted to distribute weight and to transmit forces and to rotate freely in a plane substantially perpendicular to the axis of said other one of said bones relative to said bearing surface means while distributing weight and transmitting forces thereto, and an upstanding portion fitted between the bearing elements of said first prosthesis, said upstanding portion having an opening adapted to receive a transverse support shaft;

a transverse support shaft positioned in said opening in said upstanding portion of said load bearing member and in the openings in said bearing elements of said first prosthesis, said support shaft hingedly connecting said first prosthesis to said load bearing member; and said mating engagement between said thrust bearing surface means and said bearing surface means is defined by surfaces of revolution defining an apex angle greater than an apex angle of an approximately similar conical surface of revolution of sufficient magnitude to enable free mobility.

35. A prosthetic joint for surgical implant to link two bones in a human or animal body comprising a first component including fixation means for affixing said first component to one of said bones, a second component including a stem of circular cross section, coupling means for rotatably coupling said first and second components for rotation about an axis at right angle to said stem, and a third component including a fixation means for affixing said third component to the other of said bones, said third component including means for matingly engaging said second component and for accommodating said stem to allow rotation between the second and third components about the axis of the stem independent of the relative position between the first and second components and for supporting rotary compressive forces between the second and third components.

* * * * *